US008979902B2

(12) United States Patent
Biedermann et al.

(10) Patent No.: US 8,979,902 B2
(45) Date of Patent: Mar. 17, 2015

(54) DYNAMIC STABILIZATION DEVICE FOR BONES OR VERTEBRAE

(75) Inventors: Lutz Biedermann, Villingen (DE); Wilfried Matthis, Weiswell (DE); Helmar Rapp, Deiβlingen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

(21) Appl. No.: 13/477,834

(22) Filed: May 22, 2012

(65) Prior Publication Data
US 2012/0283779 A1    Nov. 8, 2012

Related U.S. Application Data

(63) Continuation of application No. 11/645,325, filed on Dec. 21, 2006, now Pat. No. 8,192,468.

(60) Provisional application No. 60/753,772, filed on Dec. 23, 2005.

(51) Int. Cl.
*A61B 17/70* (2006.01)
(52) U.S. Cl.
CPC ......... *A61B 17/7022* (2013.01); *A61B 17/7037* (2013.01); *A61B 17/7032* (2013.01)
USPC ........... 606/257; 606/254; 606/255; 606/261; 606/266
(58) Field of Classification Search
USPC ................................. 606/246–279
See application file for complete search history.

(56) References Cited

U.S. PATENT DOCUMENTS

| 4,771,767 | A | | 9/1988 | Steffee |
| 4,887,596 | A | | 12/1989 | Sherman |
| 5,702,395 | A | | 12/1997 | Hopf |
| 5,735,850 | A | | 4/1998 | Baumgartner et al. |
| RE36,221 | E | * | 6/1999 | Breard et al. ................... 606/54 |
| 6,090,111 | A | | 7/2000 | Nichols |
| 6,315,779 | B1 | | 11/2001 | Morrison et al. |

(Continued)

FOREIGN PATENT DOCUMENTS

| CN | 1 241 127 A | 1/2000 |
| DE | 101 17 426 A1 | 10/2002 |

(Continued)

OTHER PUBLICATIONS

"Young Modulus of Elasticity for Metals and Alloys", engineeringtoolbox.com/young-modulus-d_773.html, website, Aug. 23, 2010.

(Continued)

*Primary Examiner* — Jerry Cumberledge
(74) *Attorney, Agent, or Firm* — Christie, Parker & Hale, LLP (57) ABSTRACT

A dynamic stabilization device for bones or vertebrae is provided which includes at least two bone anchoring elements, at least one connection element, connecting the bone anchoring elements. Each bone anchoring element includes a shank portion to be anchored in the bone or in the vertebra and a head portion to be connected with the connection element. The connection element is at least partly elastic and has at least one loop section. The head portion includes a recess with an opening for inserting the loop section. A securing element is provided for securing the loop section in the recess. The connection element is preferably in the form of an endless loop made of an elastomeric material.

34 Claims, 5 Drawing Sheets

(56) References Cited

U.S. PATENT DOCUMENTS

| | | |
|---|---|---|
| 6,530,926 B1 | 3/2003 | Davison |
| 6,616,669 B2 | 9/2003 | Ogilvie et al. |
| 6,648,885 B1 | 11/2003 | Friesem |
| 6,682,533 B1 | 1/2004 | Dinsdale et al. |
| 6,702,817 B2 | 3/2004 | Beger et al. |
| 6,706,044 B2 | 3/2004 | Kuslich et al. |
| 6,896,677 B1 | 5/2005 | Lin |
| 6,966,910 B2 | 11/2005 | Ritland |
| 7,507,240 B2 | 3/2009 | Olsen |
| 7,608,095 B2 | 10/2009 | Yuan et al. |
| 2001/0037111 A1 | 11/2001 | Dixon et al. |
| 2002/0007184 A1 | 1/2002 | Ogilvie et al. |
| 2002/0052603 A1 | 5/2002 | Nichols et al. |
| 2002/0133155 A1 | 9/2002 | Ferree |
| 2002/0138077 A1* | 9/2002 | Ferree .............. 606/61 |
| 2002/0143341 A1 | 10/2002 | Biedermann et al. |
| 2002/0177853 A1 | 11/2002 | Chervitz et al. |
| 2003/0023241 A1 | 1/2003 | Drewry et al. |
| 2003/0045875 A1* | 3/2003 | Bertranou et al. .............. 606/61 |
| 2003/0088251 A1* | 5/2003 | Braun .................. 606/73 |
| 2003/0125741 A1 | 7/2003 | Biedermann et al. |
| 2003/0149431 A1 | 8/2003 | Varieur |
| 2003/0171749 A1* | 9/2003 | Le Couedic et al. ............ 606/61 |
| 2003/0191470 A1 | 10/2003 | Ritland |
| 2003/0220642 A1 | 11/2003 | Freudiger |
| 2004/0006342 A1 | 1/2004 | Itarac et al. |
| 2004/0039383 A1 | 2/2004 | Jackson |
| 2004/0039386 A1 | 2/2004 | Kumar et al. |
| 2004/0097942 A1 | 5/2004 | Allen et al. |
| 2004/0111088 A1 | 6/2004 | Picetti et al. |
| 2004/0172024 A1 | 9/2004 | Gorek |
| 2004/0172025 A1 | 9/2004 | Drewry et al. |
| 2004/0254577 A1 | 12/2004 | Delecrin et al. |
| 2004/0260283 A1* | 12/2004 | Wu et al. .................. 606/61 |
| 2004/0260287 A1 | 12/2004 | Ferree |
| 2005/0010215 A1 | 1/2005 | Delecrin et al. |
| 2005/0080420 A1 | 4/2005 | Farris et al. |
| 2005/0131410 A1 | 6/2005 | Lin |
| 2005/0154388 A1 | 7/2005 | Roussouly et al. |
| 2005/0171537 A1 | 8/2005 | Mazel et al. |
| 2005/0171539 A1 | 8/2005 | Braun et al. |
| 2005/0203517 A1 | 9/2005 | Jahng et al. |
| 2005/0203518 A1 | 9/2005 | Biedermann et al. |
| 2005/0228326 A1* | 10/2005 | Kalfas et al. .................. 602/19 |
| 2005/0234451 A1 | 10/2005 | Markworth |
| 2005/0240180 A1 | 10/2005 | Vienney et al. |
| 2005/0261687 A1 | 11/2005 | Garamszegi et al. |
| 2005/0267470 A1* | 12/2005 | McBride .................. 606/61 |
| 2005/0277931 A1* | 12/2005 | Sweeney et al. .................. 606/61 |
| 2006/0064090 A1* | 3/2006 | Park .............. 606/61 |
| 2006/0282080 A1 | 12/2006 | Albert et al. |
| 2007/0288008 A1 | 12/2007 | Park |

FOREIGN PATENT DOCUMENTS

| | | |
|---|---|---|
| EP | 0669109 B1 | 8/1995 |
| EP | 1238637 B1 | 9/2002 |
| EP | 1364622 A2 | 11/2003 |
| FR | 2 806 615 A1 | 9/2001 |
| FR | 2 820 968 A1 | 8/2002 |
| FR | 2 863 860 A1 | 6/2005 |
| GB | 2 294 394 A | 5/1996 |
| GB | 2 382 304 A | 5/2003 |
| JP | 09-98983 A | 4/1997 |
| JP | 2005-502422 A | 1/2005 |
| JP | 2005-169071 A | 6/2005 |
| WO | WO 96/02199 A1 | 2/1996 |
| WO | WO 98/27884 | 7/1998 |
| WO | WO 99/52462 A2 | 10/1999 |
| WO | WO 03/039330 A2 | 5/2003 |
| WO | WO 03/094699 A2 | 11/2003 |
| WO | WO 2005/058173 A1 | 6/2005 |

OTHER PUBLICATIONS

European Search Report for European Application No. 09 00 2445, search report dated Mar. 13, 2009 and mailed Mar. 24, 2009 (5 pgs.).

European Search Report for European Application No. 05028284.7-2318 dated Apr. 26, 2006 and mailed May 8, 2006, 6 pp.

Search of the Austrian Patent Office by Serv.ip, "Ihr Partner für Forschung und Innovation Express-Recherche zum Stand der Technik," dated Mar. 13, 2006, 6 pp.

* cited by examiner

DYNAMIC STABILIZATION DEVICE FOR BONES OR VERTEBRAE

CROSS-REFERENCE TO RELATED APPLICATION(S)

This is a continuation of allowed U.S. patent application Ser. No. 11/645,325, filed Dec. 21, 2006, now U.S. Pat. No. 8,192,468, issued on Jun. 5, 2012, which claims the benefit of U.S. Provisional Patent Application Ser. No. 60/753,772, filed Dec. 23, 2005, and claims priority from European Patent Application EP05028284, filed Dec. 23, 2005, the entire disclosures of which are incorporated herein by reference.

BACKGROUND

The present disclosure relates to a dynamic stabilization device for bones or vertebrae comprising at least two bone anchoring elements which are connected by an elastic loop. The elastic loop allows a limited motion between the two bone anchoring elements and hence provides a dynamic stabilization of the two bones or vertebrae.

EP 0 669 109 B1 discloses a stabilization device comprising at least two monoaxial bone screws anchored in adjacent vertebrae and connected by a strap to transmit tensile forces between the respective vertebrae. A support body which is resistant to compression surrounds the strap between the bone screws to transmit compressive forces. The strap is fastened to the bone screws in a pre-stressed manner. If more than two bone screws are to be connected, this stabilization device is not easy to handle during surgery and the possibilities of adjusting the device are limited.

Another dynamic stabilization device comprising a bone screw and a flexible rod which is made of an elastomeric material is known from EP 1 364 622 A2. The elastic properties of the system which can be achieved between adjacent vertebrae are determined by the shape and the characteristics of the material of the rod. If a plurality of vertebrae shall be interconnected it is difficult to adapt the elastic properties over the length of the connection according to the actual requirements at the operation site. Furthermore, the receiving part and the shaft of the bone screw are monoaxially connected. This limits the possibility of adjustment of the position of the shaft relative to the rod.

US 2002/0133155 A1 discloses a spinal stabilization system with cross-coupled vertebral stabilizers incorporating spinal motion restriction. The cross-coupled members may assume different forms, including, among others, elastic bands.

U.S. Pat. No. 6,616,669 B2 discloses a device for tethering the spine which is a combination of an artificial strand threaded through channels defined in a set of blocks attached to the vertebral bodies on the convex side of the spine. The device is used to treat deformities by selectively constraining the growth in a portion of the convex side of the spine.

Based on the above, there is a need for a dynamic stabilization device for bones, in particular for vertebrae, which allows an easy adjustment according to the actual clinical requirements and which is simple and safe to be installed during surgery.

SUMMARY

The disclosed dynamic stabilization device provides a modular system comprising several endless loops with different length and/or elasticity. Accordingly, it is possible to adapt the system to the actual requirements at the operation site during surgery by simply selecting an elastic loop with appropriate size and stiffness. If a plurality of vertebrae shall be interconnected different elastic loops can be used according to the requirements for stabilization of adjacent motion segments. If the bone anchoring element is a polyaxial screw, this allows a better adjustment of the orientation of the screw head relative to the shank. In combination with the possibility of adjusting the dynamic properties of the device to the actual clinical requirements, it is therefore possible to minimize the forces acting onto the shank of the bone anchoring element. Hence, the disclosed dynamic stabilization device has an improved lifetime and a more balanced performance.

Further features and advantages of the invention will become apparent and will be best understood by reference to the following detailed description of embodiments taken in conjunction with the accompanying drawings.

DETAILED DESCRIPTION

Figure 1:
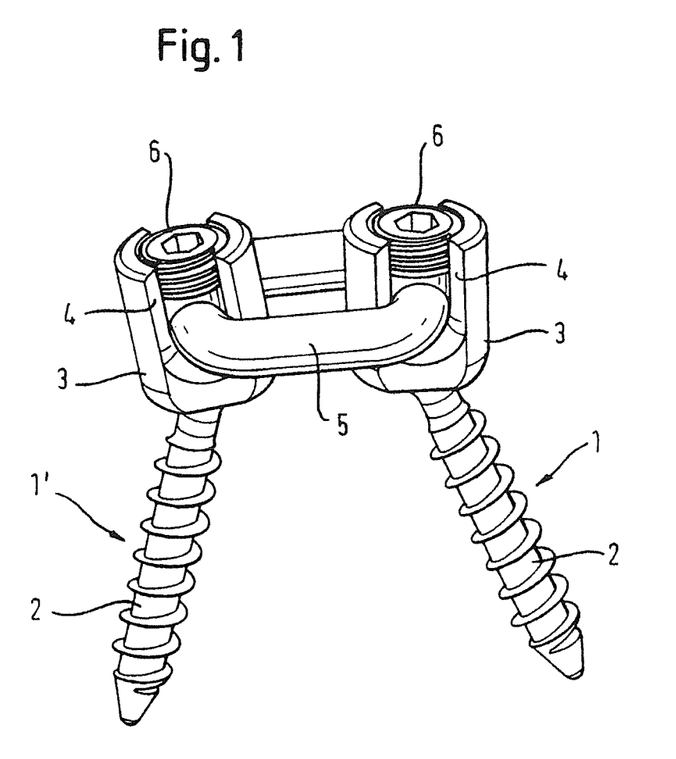
FIG. 1 shows a perspective view of a dynamic stabilization device according to a first embodiment.

A first embodiment of the dynamic stabilization device which is shown in FIG. 1 includes at least two bone anchoring elements 1, F. Each bone anchoring element 1, 1' has a shank portion 2 with a bone thread for anchoring in the bone and a receiving part 3 connected to the shank portion 2. The receiving part 3, which is also referred to herein as the head portion, has a recess 4 in which an endless elastic loop 5 is inserted so as to connect the two bone anchoring elements 1, V. A securing element 6 is provided to secure the endless elastic loop 5 in the receiving part 3 of the bone anchoring element 1, 1'.

Figure 2:
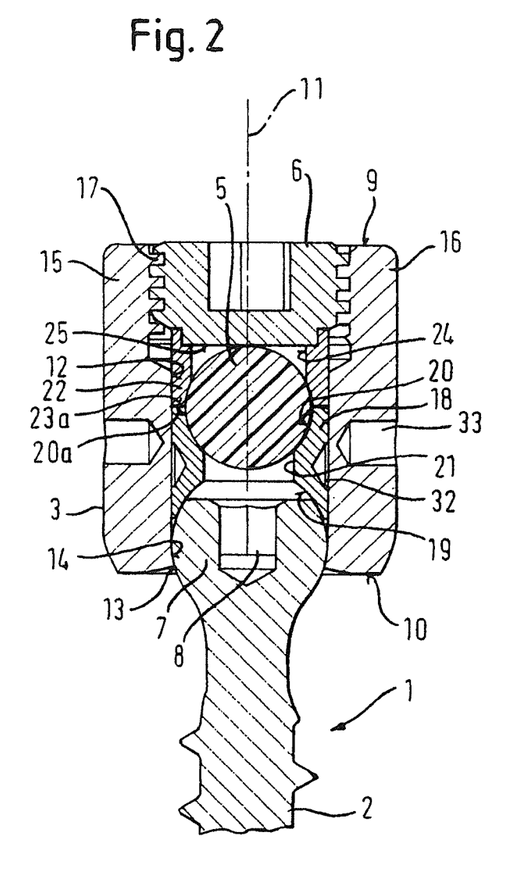
FIG. 2 shows a sectional view of a bone anchoring element of the dynamic stabilization device according to the first embodiment with the elastic loop inserted.
Figure 3:
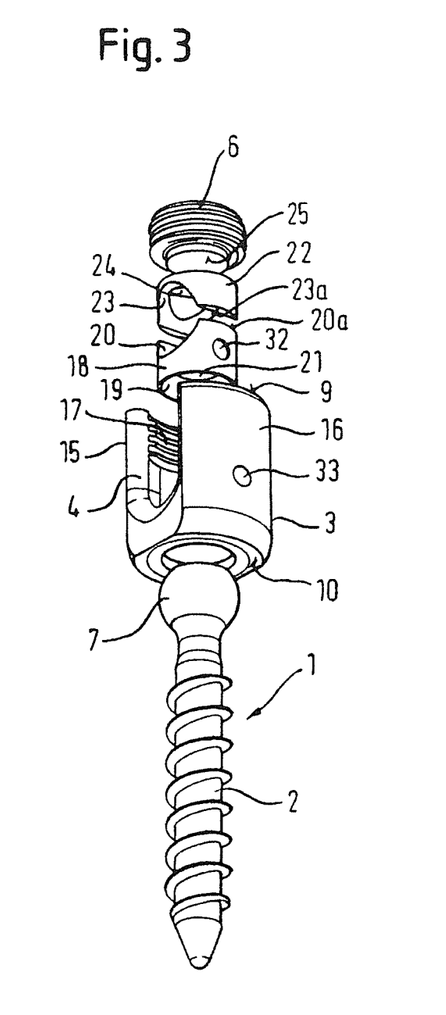
FIG. 3 shows an exploded perspective view of the bone anchoring element according to FIG. 2.

As can be seen from FIGS. 1 to 3, the bone anchoring element 1 has at one end of the shank portion 2 and a head 7 which is in this embodiment shaped as a spherical segment. At the side opposite to the shank 2, the spherical head 7 has a recess 8 for engagement with a screwing-in tool.

The receiving part 3 comprises a first end 9 and a second end 10 opposite to the first end and a longitudinal axis 11 intersecting plane of the first end and a second end. Coaxially with the longitudinal axis 11 a bore 12 is provided which extends from the first end 9 to a predetermined distance from the second end 10. At the second end 10 an opening 13 is provided the diameter of which is smaller than the diameter of the bore 12. A spherical section 14 is provided adjacent to the opening 13 which forms a seat for the spherical head 7. The section 14 needs not to be a spherical section, but can have another shape such as, for example, a conically tapering shape.

The recess 4 in the receiving part 3 is U-shaped starting at the first end 9 and extending in the direction of the second end 10 to a predetermined distance from the second end. By means of the U-shaped recess 4 two free legs 15, 16 are formed extending towards the first end 9. Adjacent to the first end 9, the receiving part 3 comprises an internal thread 17 on the legs 15, 16.

The bone anchoring element further includes a first pressure element 18 which has a cylindrical construction with an outer diameter which is only slightly smaller than the inner diameter of the bore 12 to allow the first pressure element 18 to be introduced into the bore 12 of the receiving part 3 and to be moved in the axial direction. On its lower side facing the second end 10, the pressure element 18 includes a spherical recess 19 the radius of which corresponds to the radius of the spherical head 7 of the bone screw. On the opposite side, the first pressure element 18 has a cylindrical recess 20 which extends transversely to the longitudinal axis 11. The lateral diameter of this recess 20 is selected such that the loop 5, which has a circular cross section, can be inserted into the recess 20. The depth of this cylindrical recess 20 is selected such that in an assembled state when the loop 5 is inserted and pressed in the direction of the bottom of the U-shaped recess 4, the first pressure element 18 exerts a pressure onto the head 7. Preferably, the depth of the cylindrical recess 20 is about half of the diameter of the loop 5. The first pressure element 18 further has a coaxial bore 21 for guiding through a screwing-in tool.

The bone anchoring element further comprises a second pressure element 22 with a cylindrical construction with an outer diameter corresponding to the outer diameter of the first pressure element 18 so as to be slidable in the bore 12. The second pressure element 22 has a cylindrical recess 23 on its side facing the first pressure element 18. The diameter of the cylindrical recess 23 is such that the loop 5 can fit therein and its depth is half or less than half of the diameter of the loop 5. Furthermore, the second pressure element 22 also comprises a coaxial bore 24. In an assembled state, as shown in FIG. 2, the first pressure element 18 and the second pressure element 22 encompass the loop 5. As can be seen in particular in FIGS. 2 and 3, the first pressure element 18 and the second pressure element 22 are inserted into the receiving part 3 in such a manner that the orientation of the cylindrical recesses 20 and 23 corresponds to the orientation of the U-shaped recess 4 an upper edge 27a of the first pressure element 18 abuts a lower edge 29a of the second pressure element 22. Hence, the loop 5 is clamped between the first pressure element 18 and the second pressure element 22.

The securing element 6 is in the embodiment shown formed as an inner screw which can be screwed-in between the legs 15, 16. On its side facing the receiving part 3, the inner screw 6 has a projection 25 which fits into the coaxial bore 24 of the second pressure element 22. In the assembled state shown in FIG. 2, the projection 25 contacts the loop 5. The internal thread 17 and the cooperating thread of the inner screw 6 can have any known thread shape. Using a flat thread or a negative angle thread, however, prevents splaying of the legs 15,16.

The receiving part 3 and the pressure element 18 can be loosely pre-assembled by means of crimp bores 32, 33 provided on opposite sides on the receiving part 3 and the first pressure element 18, respectively.

The bone anchoring device can be made of biocompatible material such as stainless steel or titanium or any other material suitable for bone screws.

Figures 5, 6, 7:
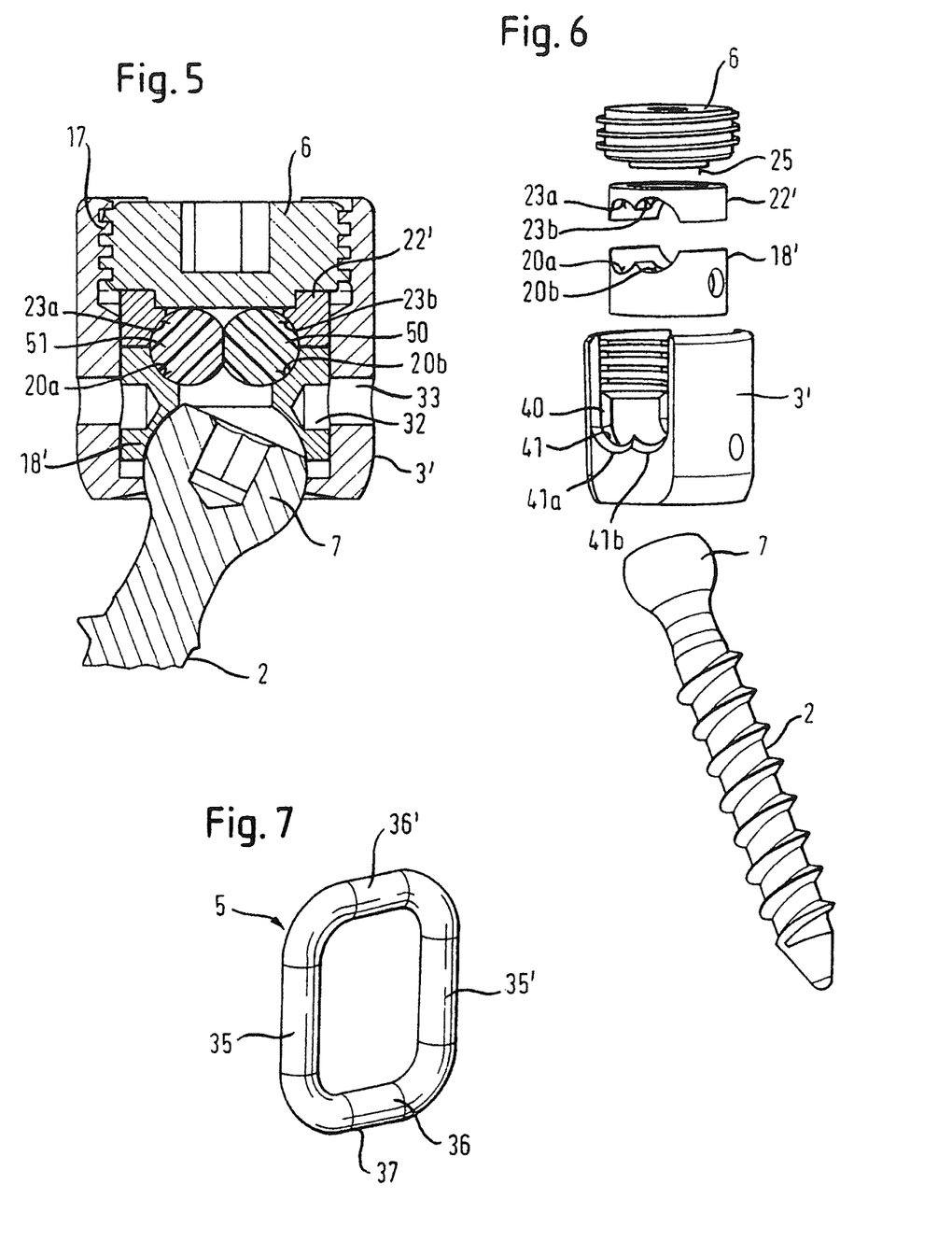
FIG. 5 shows a sectional view of a bone anchoring element according to the second embodiment with the elastic loops inserted.
FIG. 6 shows an exploded view of the bone anchoring element of the dynamic stabilization device of the second embodiment without the elastic loops.
FIG. 7 shows a modification of the elastic loop.

As can be seen in FIGS. 1 and 7, the loop 5 is endless and has a substantially rectangular contour with two opposing long sides 35, 35' and two opposing short sides 36, 36'. The length of the short sides 36, 36' is slightly larger than the diameter of the receiving part 3 so that the short sides 36, 36' can be inserted into the U-shaped recess 4 of the receiving part 3. The length of the long sides 35, 35' corresponds to the distance between the receiving parts of the two anchoring elements on the operation site. The loop 5 is preferably made of an elastomeric material, such as a biocompatible plastic material, for example a polymer on the basis of polyurethane, polysilicone or PEEK. A particularly suitable material is Polycarbonate Urethane. It is fully or partially flexible. In particular, the long sides 35, 35' are flexible. In order to avoid abrasion, the loop 5 can have a reinforcing or protective structure 37 on the short sides 36, 36' and/or on the long sides 35, 35'. The loop 5 preferably has a circular cross section.

A plurality of loops can be provided with varying dimensions such as a varying length and/or a varying diameter. They also can vary in their elastic properties.

In use, at least two bone anchoring devices 1, 1' are anchored in two bone fragments or two vertebrae which shall be dynamically stabilized. The bone anchoring devices 1, 1' consist of the pre-assembled bone screw, receiving part and first pressure element 18. Then, the loop 5 is inserted in the receiving parts 3 of the bone anchoring elements so as to connect the receiving parts 3. Next, the second pressure element 22 is inserted in each of the receiving parts 3 to encompass the loop 5. Thereafter, the inner screw 6 is screwed-in between the legs 15, 16 of the receiving part 3. In this condition, the inner screw 6 prevents falling-out of the second pressure element 23 while the receiving part 3 is still pivotable with respect to shank 2. When tightening the inner screw 6, it presses onto the second pressure element 22 which itself presses onto the first pressure element 18 to exert a pressure onto the head 7 of the bone screw to lock the head 7 of the bone screw in its angular position. The loop 5 usually is inserted in a non-stressed condition.

The required dynamic properties of the device can be easily adjusted by selecting the loop 5 which has the appropriate size and stiffness. If a loop 5 is selected which is highly flexible, it may transmit tensile forces only. If a loop 5 is selected which has a high stiffness, it may also be able to transmit compressive and bending forces.

It is also possible to insert the loop 5 in a pre-stressed manner.

Figure 4:
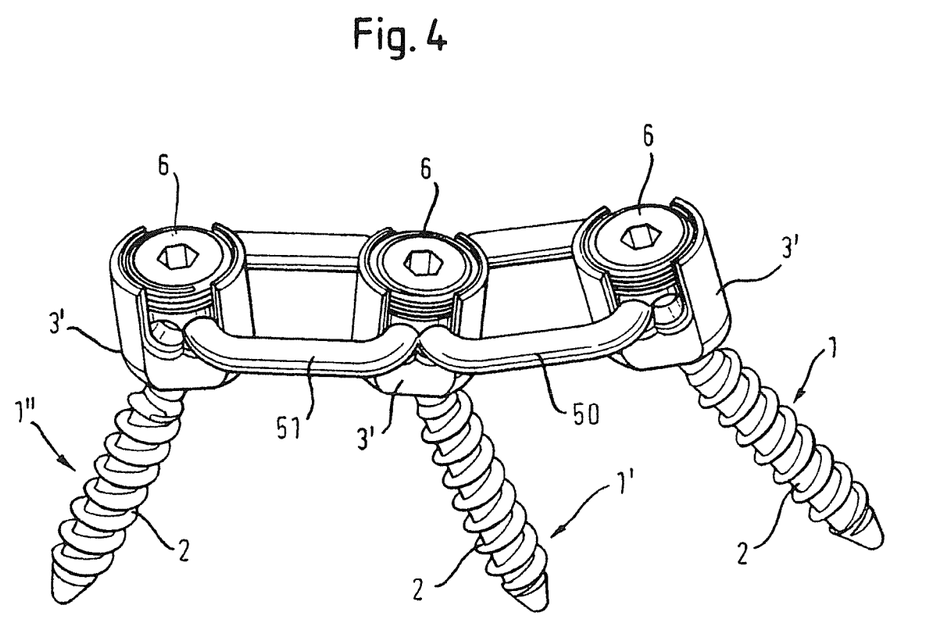
FIG. 4 shows a dynamic stabilization device according to a second embodiment.

A second embodiment is shown in FIGS. 4 to 6. The second embodiment differs from the first embodiment in that it allows insertion of two or more loops in order to connect more than two anchoring elements. In the example shown in FIG. 4 three anchoring elements 1, 1', 1'' are connected by two endless elastic loops 50, 51, for example, to stabilize two motion segments of the spinal column.

Parts of the second embodiment which are identical to those of the first embodiment are characterized with the same reference numbers and the description thereof will not be repeated. The receiving part 3 has a recess 40 which is similar to two U-shaped recesses which are combined. The bottom 41 of the recess 40 therefore has two partially cylindrical sections 41a, 41b which are adjacent to each other in such a manner that the two loops 50, 51 can be separately accommodated in the sections 41a, 41b. The first pressure element 18' differs from the first pressure element 18 of the first embodiment in that instead of one single cylindrical recess 20 there are two adjacent cylindrical recesses 20a, 20b to receive the two separate loops 50, 51. Correspondingly, the second pressure element 22' has instead of one single cylindrical recess on its side facing the first pressure element to separate cylindrical recesses 23a, 23b in order to cover and encompass the two loops 50, 51.

In use, the procedure of anchoring the bone anchoring element and inserting the loops is the same as with the first embodiment. It is however possible with this embodiment to connect more than two bone anchoring devices as shown in FIG. 4. If three bone anchoring devices shall be connected the central bone anchoring device 1', receives two loops. In this manner, it is possible to connect several motion segments of the spinal column using the appropriate loops required for each motion segment. If more than two adjacent vertebrae shall be stabilized, the receiving parts of the bone screws which are positioned at the respective ends of the chain can be adapted to accommodate only one single loop as those shown in FIGS. 1 to 3. This modular system allows to precisely adapt the dynamic stabilization device to the respective motion segment. The system is easy to handle, since the surgeon has only to select the appropriate loop and insert the loop into the receiving part and fix it. It is even possible to use conventional polyaxial bone screws. Only the first pressure element 18, 18' and second pressure element 22, 22' are adapted to receive the loops and the loops themselves have to be provided in addition to the conventional equipment.

In a further embodiment it is possible to add an elastomeric damper (not shown) which surrounds at least one of the long sides of a loop to maintain distance between the receiving parts 3 in a case where the loops are flexible to a greater extent.

Modifications of the invention are possible. The loop does not have to have a circular cross section. It can have an oval, rectangular or square cross-section or a cross-section of another shape. The loop also can have a cross-section varying over the length of the sides, in particular over the length of the long sides. In addition, the contour needs not to be rectangular, as shown in the Figures, but can be oval or can have another shape. The loops can be highly flexible or hardly flexible. The surface needs not to be smooth, it can be textured or structured.

Figure 8:
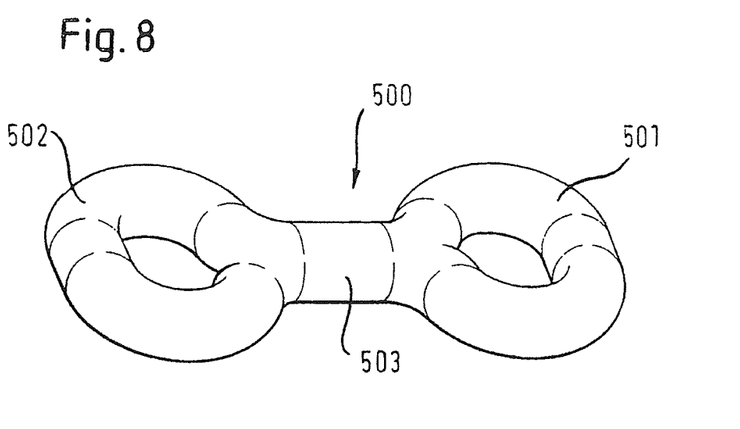
FIG. 8 shows a second embodiment of the elastic loop in a perspective view.

FIG. 8 shows a second embodiment of the endless elastic loop. The loop 500 comprises a first closed loop section 501 and a second closed loop section 502 which are connected by a straight section 503. The loop 500 is connected via the first and second loop closed loop sections 501 and 502 with the corresponding receiving parts 3 of the bone screws. The loop 500 is made of an elastomeric material. In a modification, only the straight section 503 is elastic while the closed loop section 501 and 502 are stiff. The loop 500 can also have reinforcing structures to prevent abrasion.

Figure 9:
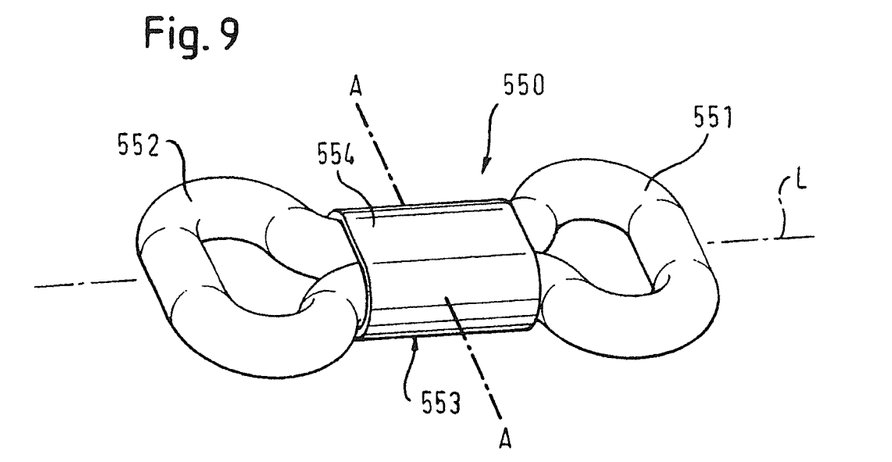
FIG. 9 shows a modification of the second embodiment of the elastic loop in a perspective view.
Figure 10:
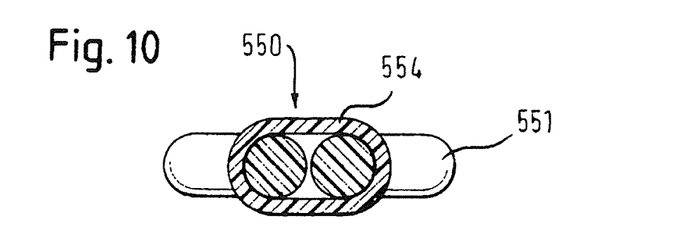
FIG. 10 shows a sectional view of the elastic loop of FIG. 9 in a plane extending in a perpendicular direction to the longitudinal axis L of the loop along A-A.

In FIGS. 9 and 10 a further modification of the loop 5, 50, 51 as shown in FIGS. 1 to 4 is shown. The loop 550 comprises two end sections 551 and a central section 553 formed by the two long sides which are drawn together by means of sleeve 554. As a result thereof, the loop 550 resembles the loop 500 shown in FIG. 8 having the two closed loop end sections 501, 502. The sleeve 554 can be made of an elastomeric material.

The loop needs not to be tightly clamped between the first pressure element 18, 18' and the second pressure element 22, 22'. It is also possible that the loops are only loosely held between the first pressure element 18, 18' and the second pressure element 22, 22'. In a further modification the cylindrical recess of the first and/or the second pressure element can have projections (not shown), preferably extending transversely to the cylinder axis. The projections can press onto the surface of the loop in such a way that material of the loop flows, thus creating a form-fit connection. For the inner screw 6 all known modifications can be used. This includes also the use of an outer ring or nut.

In the embodiment described the screw is introduced from the top into the receiving part 3. However, a screw can also be introduced from the bottom of the receiving part if the receiving part 3 is constructed to allow this.

In a further modification, the receiving part 3 and the shank 2 can be rigidly connected thus presenting a monoaxial screw. In this case, the first pressure element 18, 18' can be omitted. In a further modification also the second pressure element 22, 22' can be omitted.

In a further modification the recess 4, 40 is not open to the top of the receiving part 3 but to the lateral side.

The invention is not limited to screws as bone anchoring elements but can be realized with bone hooks or any other bone anchoring element.

While a particular form of the disclosure has been illustrated and described, it will be apparent that various modifications can be made without departing from the spirit and scope of the disclosure. Accordingly, it is not intended that the disclosure be limited, except as by the appended claims.

What is claimed is:

1. A dynamic stabilization device for bones or vertebrae comprising:
   at least two bone anchoring elements each having a shank portion to be anchored to a bone or vertebra and a head portion with a recess forming two opposing openings in a side wall of the head portion, such that an axis of the recess extends from one of the openings to the other one of the openings;
   one or more connection elements configured to be inserted into the recess of each of the bone anchoring elements; and
   a securing element for each bone anchoring element;
   wherein a first connection element from among the one or more connection elements is monolithic and comprises an elastomer material so as to be at least partly elastic, and is an endless loop that has a first end for connecting to one of the bone anchoring elements, a second end for connecting to another one of the bone anchoring elements, and a longitudinal axis extending from the first end to the second end;
   wherein the recess of at least one of the bone anchoring elements is configured for inserting the loop; and
   wherein when the first connection element is connected with the bone anchoring elements, the securing elements secure respective portions of the first connection element in the recess of each respective bone anchoring element, and the axes of the recesses of the bone anchoring elements are transverse to the longitudinal axis of the first connection element.

2. The dynamic stabilization device according to claim 1, wherein an inner wall of the head portion of each of the bone anchoring elements defines the corresponding recess and comprises an inner thread, and wherein the securing element is a screw to be screwed into the recess.

3. The dynamic stabilization device according to claim 1, Wherein a pressure element is configured to be provided between the securing element and the first connection element for at least one of the bone anchoring elements to exert a pressure onto the first connection element via the action of the securing element.

4. The dynamic stabilization device according to claim 1, wherein the recess is shaped so as to accommodate a single loop.

5. The dynamic stabilization device according to claim 1, wherein the recess is shaped so as to accommodate at least two loops.

6. The dynamic stabilization device according to claim 1, wherein the shank portion and the head portion are rigidly connected.

7. The dynamic stabilization device according to claim 1, wherein the shank portion and the head portion are pivotably connected.

8. The dynamic stabilization device according to claim 7, wherein the shank portion has a spherically shaped head which is pivotably held in the head portion.

9. The dynamic stabilization device according to claim 7, wherein for at least one of the bone anchoring elements, a first pressure element and a second pressure element are provided which are configured to encompass the first connection element in the recess and which are slideable in the recess, such that when applying a pressure via the securing element, an angular position of the shank is locked.

10. The dynamic stabilization device according to claim 9, wherein the first pressure element exerts a pressure on the spherically shaped head.

11. The dynamic stabilization device according to claim 1, wherein a cross-section of the loop is substantially circular.

12. The dynamic stabilization device according to claim 1, wherein the first connection element is connected to two bone anchoring elements in a non-stressed condition.

13. The dynamic stabilization device of claim 1, wherein the recess is substantially U-shaped.

14. The dynamic stabilization device according to claim 1, wherein a part of the head portion of at least one of the bone anchoring elements is configured to extend into an internal space of the loop.

15. The dynamic stabilization device according to claim 1, wherein the first connection element is a single loop.

16. The dynamic stabilization device according to claim 1, further comprising a sleeve around the first connection element for dividing the loop into two separate loop sections.

17. A dynamic stabilization device for bones and vertebrae comprising:
one or more monolithic connection elements each comprising an elastic material and having a first end, a second end, a longitudinal axis extending from the first end to the second end, and at least one loop, wherein a first connection element from among the connection elements is a double loop having two closed loops and a central section therebetween; and
at least two bone anchoring elements, each bone anchoring element comprising:
a shank portion configured to be anchored in a bone or in a vertebra;
a head portion having a recess configured to receive a portion of the first connection element, the recess forming two opposing openings in a side wall of the head portion, such that an axis of the recess extends from one of the openings to the other one of the openings;
a pressure element mountable in the recess over the portion of the first connection element in the recess; and
a securing element configured to secure the portion of the first connection element in the recess by pressure exerted with the pressure element;
wherein the bone anchoring elements are configured to be connected to the first end and the second end of the first connection element, respectively, such that the axes of the recesses of the bone anchoring elements are transverse to the longitudinal axis of the first connection element, and wherein the recess of at least one of the bone anchoring elements engages one of the loops of the first connection element.

18. The dynamic stabilization device according to claim 17, wherein the recess and the pressure element are shaped so as to accommodate at least two loops of two separate connection elements, respectively.

19. The dynamic stabilization device according to claim 17, wherein the shank portion and the head portion are pivotably connected.

20. The dynamic stabilization device according to claim 19, further comprising a second pressure element configured to mount under the portion of the first connection element in the recess, wherein securing the securing element further exerts pressure on the second pressure element to lock an angular position of the shank relative to the head portion.

21. A dynamic stabilization device for bones or vertebrae comprising:
at least two bone anchoring elements each having a shank portion to be anchored to a bone or vertebra and a head portion with a recess forming two opposing openings in a side wall of the head portion, such that an axis of the recess extends from one of the openings to the other one of the openings;
one or more connection elements configured to be inserted into the recess of each of the bone anchoring elements; and
a securing element for each bone anchoring element;
wherein a first connection element from among the one or more connection elements is a double loop having two closed loops and a central section therebetween, is monolithic and at least partly elastic, and has a first end for connecting to one of the bone anchoring elements, a second end for connecting to another one of the bone anchoring elements, and a longitudinal axis extending from the first end to the second end;
wherein the recess of at least one of the bone anchoring elements is configured for inserting one of the loops; and
wherein when the first connection element is connected with the bone anchoring elements, the securing elements secure respective portions of the first connection element in the recess of each respective bone anchoring element, and the axes of the recesses of the bone anchoring elements are transverse to the longitudinal axis of the first connection element.

22. The dynamic stabilization device according to claim 21, Wherein an inner wall of the head portion of each of the bone anchoring elements defines the corresponding recess and comprises an inner thread, and wherein the securing element is a screw to be screwed into the recess.

23. The dynamic stabilization device according to claim 21, wherein a pressure element is configured to be provided between the securing element and the first connection element for at least one of the bone anchoring elements to exert a pressure onto the first connection element via the action of the securing element.

24. The dynamic stabilization device according to claim 21, wherein the recess is shaped so as to accommodate a single loop.

25. The dynamic stabilization device according to claim 21, wherein the recess is shaped so as to accommodate at least two loops.

26. The dynamic stabilization device according to claim 21, wherein the shank portion and the head portion are rigidly connected.

27. The dynamic stabilization device according to claim 21, wherein the shank portion and the head portion are pivotably connected.

28. The dynamic stabilization device according to claim 27, wherein the shank portion has a spherically shaped head which is pivotably held in the head portion.

29. The dynamic stabilization device according to claim 27, wherein for at least one of the bone anchoring elements, a first pressure element and a second pressure element are provided which are configured to encompass the first connection element in the recess and which are slideable in the recess, such that when applying a pressure via the securing element, an angular position of the shank is locked.

30. The dynamic stabilization device according to claim 29, wherein the first pressure element exerts a pressure on the spherically shaped head.

31. The dynamic stabilization device according to claim 21, wherein a cross-section of at least one of the loops is substantially circular.

32. The dynamic stabilization device according to claim 21, wherein the first connection element is connected to two bone anchoring elements in a non-stressed condition.

33. The dynamic stabilization device of claim 21, wherein the recess is substantially U-shaped.

34. The dynamic stabilization device according to claim 21, wherein a part of the head portion of at least one of the bone anchoring elements is configured to extend into an internal space of one of the loops.

* * * * *

UNITED STATES PATENT AND TRADEMARK OFFICE
CERTIFICATE OF CORRECTION

Page 1 of 1

PATENT NO. : 8,979,902 B2
APPLICATION NO. : 13/477834
DATED : March 17, 2015
INVENTOR(S) : Lutz Biedermann et al.

It is certified that error appears in the above-identified patent and that said Letters Patent is hereby corrected as shown below:

On the Title Page

(75) Inventors: Delete "Villingen"
Insert -- VS-Villingen --

Delete "Weiswell"
Insert -- Weisweil --

In the Specification

Column 2, DETAILED DESCRIPTION, line 48
Delete "F."
Insert -- 1'. --

Column 2, DETAILED DESCRIPTION, line 53
Delete "V."
Insert -- 1'. --

In the Claims

Column 6, Claim 3, line 60
Delete "Wherein"
Insert -- wherein --

Column 8, Claim 22, line 48
Delete "Wherein"
Insert -- wherein --

Signed and Sealed this
Twenty-sixth Day of January, 2016

Michelle K. Lee
*Director of the United States Patent and Trademark Office*